United States Patent
Shirakawa et al.

(10) Patent No.: US 8,097,138 B2
(45) Date of Patent: Jan. 17, 2012

(54) OXYGEN PARTIAL PRESSURE CONTROL APPARATUSES AND METHODS OF USING SOLID ELECTROLYTES FOR OXYGEN PARTIAL PRESSURE CONTROL

(75) Inventors: Naoki Shirakawa, Tsukuba (JP);
Shinichi Ikeda, Tsukuba (JP);
Katsuhide Uchida, Hitachinaka (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 1012 days.

(21) Appl. No.: 11/597,045

(22) PCT Filed: May 19, 2005

(86) PCT No.: PCT/JP2005/009178
§ 371 (c)(1),
(2), (4) Date: Nov. 8, 2007

(87) PCT Pub. No.: WO2005/111270
PCT Pub. Date: Nov. 24, 2005

(65) Prior Publication Data
US 2008/0217187 A1    Sep. 11, 2008

(30) Foreign Application Priority Data

May 19, 2004  (JP) .................................. 2004-149281

(51) Int. Cl.
*G01N 27/41* (2006.01)
*G01N 27/419* (2006.01)

(52) U.S. Cl. ........ 204/425; 204/410; 204/411; 204/424; 205/783.5

(58) Field of Classification Search .......... 204/400–435, 204/228.6, 265; 205/775–794.5, 634; 73/23.1–23.32
See application file for complete search history.

(56) References Cited

U.S. PATENT DOCUMENTS

| | | | | |
|---|---|---|---|---|
| 3,699,032 A | * | 10/1972 | Rapp | 422/82.01 |
| 3,772,177 A | * | 11/1973 | Rittiger et al. | 204/422 |
| 4,178,222 A | * | 12/1979 | Murphy et al. | 204/409 |
| 4,181,583 A | * | 1/1980 | Steiger et al. | 205/396 |
| 4,601,809 A | * | 7/1986 | Kitahara | 204/406 |
| 5,332,483 A | | 7/1994 | Gordon | 204/265 |

(Continued)

FOREIGN PATENT DOCUMENTS

DE          695 18517 T2      6/2001

(Continued)

*Primary Examiner* — Kaj K Olsen
*Assistant Examiner* — Susan Thai
(74) *Attorney, Agent, or Firm* — Medlen & Carroll, LLP

(57) ABSTRACT

The present invention provides oxygen partial pressure control apparatuses that can control the partial pressure of oxygen in atmospheric gases in processing apparatuses or the like to within the range of 0.2 to $10^{-30}$ atm, while maintaining low material and operational cost conditions. The present invention provides oxygen partial pressure control apparatuses in which air or pure oxygen is supplied to the inside of a heating furnace that can heat and maintain solid electrolytes at an operational temperature, wherein the heating furnace houses at least one oxygen pump comprising a solid electrolyte with a tubular structure and at least two oxygen sensors comprising a solid electrolyte with a tubular structure, wherein the at least one oxygen pump described above and the at least two oxygen sensors described above are placed in parallel such that the aforementioned air or pure oxygen serves as a purge gas that sweeps the surroundings of each solid electrolyte tube, and wherein they are connected such that a common process gas can flow through each solid electrolyte tube.

5 Claims, 6 Drawing Sheets

U.S. PATENT DOCUMENTS

| | | | |
|---|---|---|---|
| 6,551,499 B1 | 4/2003 | Springhorn et al. | 205/784.5 |
| 2004/0222094 A1* | 11/2004 | Ieda et al. | 204/424 |
| 2005/0282051 A1* | 12/2005 | Zhou | 429/32 |

FOREIGN PATENT DOCUMENTS

| | | |
|---|---|---|
| EP | 0 766 752 B1 | 4/1997 |
| JP | 53-52194 | 5/1978 |
| JP | 55-136101 | 10/1980 |
| JP | 60-187854 | 9/1985 |
| JP | 62-138745 | 6/1987 |
| JP | 10-500450 | 1/1998 |
| JP | 2001-114589 | 4/2001 |
| JP | 2002-326887 | 11/2002 |
| JP | 2003-510588 | 3/2003 |
| JP | 2004-250283 | 9/2004 |
| WO | WO 95/27810 | 10/1995 |

* cited by examiner

OXYGEN PARTIAL PRESSURE CONTROL APPARATUSES AND METHODS OF USING SOLID ELECTROLYTES FOR OXYGEN PARTIAL PRESSURE CONTROL

This application is a U.S. national entry of International Application No. PCT/JP2005/009178, filed on May 19, 2005, which claims priority to Japanese Patent Application No. 2004-149281, filed on May 19, 2004.

TECHNICAL FIELD

The present invention relates to oxygen partial pressure control apparatuses that can supply gases whose oxygen partial pressure is controlled within the range of 0.2 to $10^{-30}$ atm. In particular, the present invention relates to electrochemical oxygen partial pressure control apparatuses that can control the partial pressure of oxygen in atmospheric gases in processing apparatuses or the like to within the range of 0.2 to $10^{-30}$ atm, while under low material and operational costs conditions. The present invention also relates to methods of using solid electrolytes to prolong the life of the oxygen partial pressure control apparatuses.

BACKGROUND ART

Methods for producing single crystal samples using atmospheric gases whose oxygen partial pressure is controlled using electrochemical oxygen pumps comprising solid electrolytes are known. Specifically, in these techniques, long, cylindrical solid electrolytes are sealed at both ends and provided with net-like platinum electrodes on portions of both the inner and outer surfaces of the cylinder's periphery. In using the sealed cylindrical solid electrolytes as oxygen pumps, inert gas is supplied into the solid electrolyte and a voltage is applied to both electrodes, which removes oxygen from within the aforementioned inert gas to the outside of the solid electrolyte and reduces the partial pressure of oxygen in the inert gas (see Patent Document 1).

The present inventors further propose improved techniques in which, as a mechanism for recycling waste gas, a conductance means and exhaust-speed varying means are installed in a return path from a sample producing apparatus. Further, the present inventors propose that by maintaining a positive pressure in the oxygen pump, contamination resulting from mixture with external gases or the like is prevented (see the specification and drawings attached to Japanese Patent Application No. 2003-42403).

Oxygen pumps which comprise solid electrolyte materials such as strontium-doped lanthanum manganate and which comprise cylindrical structures such as honeycomb structures are also known, where such oxygen pumps produce atmospheric gases with oxygen pressures ranging from high to very-low, preventing damage using feedback control of operational voltage and the like on the basis of oxygen partial pressure values from a sensor (see Patent Document 2).

Floating zone apparatuses in which a number of gas supply circuits are connected in parallel are known, where each circuit is provided with a mass flow controller such that the atmosphere can be varied over a wide range in order to adjust to variations in vapor pressure (see Patent Document 3).

Methods are also known which reuse electrochemical oxygen sensors that monitor exhaust gases from internal engines, by applying a voltage equal to or greater than a saturation voltage (see Patent Document 4).

[Patent Document 1] Japanese Patent Application Kokai Publication No. (JP-A) 2002-326887 (unexamined, published Japanese patent application).
[Patent Document 2] Japanese Patent Kohyo Publication No. (JP-A) H10-500450 (unexamined Japanese national phase publication corresponding to a non-Japanese international publication).
[Patent Document 3] Japanese Patent Application Kokai Publication No. (JP-A) 2001-114589 (unexamined, published Japanese patent application).
[Patent Document 4] Japanese Patent Kohyo Publication No. (JP-A) 2003-510588 (unexamined Japanese national phase publication corresponding to a non-Japanese international publication).

DISCLOSURE OF THE INVENTION

Problems to be Solved by the Invention

In the specification and drawings attached to the application of Japanese Patent Application No. 2003-42403, which is an improved technique of the aforementioned Patent Document 1, problems were found in the systems comprising oxygen pumps with a circulating mechanism; specifically, although such systems can reduce the oxygen partial pressure to about $10^{-30}$ atm, continuous operation under such very low oxygen conditions causes damage to zirconium tubes, which are solid electrolytes, within about a week to ten days.

Operation in a region of very low oxygen partial pressure of about $10^{-30}$ atm is expected to require a system comprising an oxygen pump with a circulating mechanism as exemplified in, for example, the specification and drawings of Japanese Patent Application No. 2003-42403. This requires not only one zirconium tube for the oxygen pump, but another two zirconium tubes for the oxygen sensor that controls oxygen partial pressure. The material costs for the zirconium tubes are thus increased, and further, since a heating furnace is required for each zirconium tube in order to raise its temperature to operational temperature as a solid electrolyte, both the costs of apparatus and of operations are increased, which is problematic.

Further, for airtight piping to the zirconium tubes, sealing mechanisms such as O-rings or bellows must be attached using adhesives able to preserve airtight conditions. However, since these sealing mechanisms are not sufficiently heat-resistant, the length of each zirconium tube must be increased such that the exposed portion protruding from the heating furnace is longer and the sealing is thus carried out in a low temperature region. Therefore, another problem arises in that the increased length of zirconium tube further increases the cost of materials and the size of the apparatus.

On the other hand, as exemplified in the aforementioned Patent Document 2, to control the oxygen partial pressure of a used gas to a predetermined accuracy, it is preferable to carry out feedback control based on oxygen sensor outputs, even for normal operations of the oxygen pump. However, for the first time, the present inventors adopted PID-controlled oxygen pumps as a driving control. Further, the level of oxygen partial pressure required for operation ranged widely, from 0.2 atm to $10^{-30}$ atm, and the control system exhibited an inherent gain-curve characteristic that depended on the oxygen partial pressure. Thus, simply incorporating a conventional fixed PID control apparatus into the oxygen pump did not provide sufficient control, and this is one factor that increased operational costs. Further, determining the gain-curve characteristics corresponding to individual operation conditions was also extremely labor intensive.

Moreover, since conventional oxygen partial pressure control apparatuses have to date been provided on the assumption that they are used for processing apparatuses whose internal volume is less than 1 L, they are unsuitable for the manufacture of mass produced products such as semiconductors, which require large volumes of gas. As exemplified in the aforementioned Patent Document 3, a number of oxygen partial pressure control apparatuses can be connected in parallel to provide sufficient supply ability. However, this is expected to increase facility and operation costs.

The method for recovering solid electrolytes exemplified in the aforementioned Patent Document 4 deals only with the reduced performance of the oxygen sensors. Application of this method to an over-reduced oxygen pump further reduces the life of the apparatus, and thus this method does not contribute to reducing facility costs or the like.

Means to Solve the Problems

To solve the various problems outlined above, the present inventors improved both the structure of apparatuses such as the oxygen pumps, and the operational methods, and thus generated an invention capable of extremely practical processing abilities and low cost operation. The present invention comprises the following technical items:

(1) an oxygen partial pressure control apparatus comprising:
at least one oxygen pump comprising a solid electrolyte with a tubular structure,
at least two oxygen sensors comprising a solid electrolyte with a tubular structure, and
a heating furnace which houses the oxygen pump and the oxygen sensors and which can heat and maintain each solid electrolyte at an operational temperature, and wherein air or pure oxygen is supplied to the inside of the heating furnace,
wherein the oxygen pump and the oxygen sensors are placed in parallel, such that the air or pure oxygen serves as a purge gas that sweeps the surroundings of each solid electrolyte tube, and they are connected such that a common process gas can flow through each solid electrolyte tube, and
wherein the oxygen partial pressure control apparatus is further electrically connected to an oxygen pump operation control means for controlling operation of the oxygen pump based on the oxygen partial pressure detected by the oxygen sensors;

(2) the oxygen partial pressure control apparatus of (1), wherein the oxygen pump comprises a solid electrolyte with a tubular structure, and wherein both ends of the solid electrolyte protrude from the heating furnace and are sealed with a sealing means to make the tube airtight, and further comprising a cooling means for cooling the sealing means;

(3) the oxygen partial pressure control apparatus of (1) or (2), wherein the oxygen sensor comprises a porous electrode formed over an entire inner surface of a tube, and a porous electrode formed as a band around an outer periphery of a tube, and wherein the sensor measures an oxygen partial pressure by detecting a difference in potential produced between the two electrodes;

(4) the oxygen partial pressure control apparatus of any of (1) to (3), wherein the oxygen pump operation control means has a PID constant defined as a function of the oxygen partial pressure, and every time the oxygen sensor samples a current oxygen partial pressure value, the value is automatically adjusted in coordination with the function, and wherein operation of the oxygen pump is subjected to PID control based on the adjusted PID constant;

(5) the oxygen partial pressure control apparatus of any of (1) to (4), wherein the heating furnace comprises at least one cylindrical resistive heating element placed in parallel with each of the solid electrolytes, wherein the ratio between the number of solid electrolytes and the number of resistive heating elements is ⅓ to 6;

(6) the oxygen partial pressure control apparatus of (5), comprising solid electrolytes arranged at equal intervals such that the axis of each solid electrolyte is located at each vertex of a honeycomb structure centered on an axis of the resistive heating element, as viewed in an axial direction of the resistive heating element and the solid electrolytes;

(7) a method for using a solid electrolyte for oxygen partial pressure control, comprising at least:
a step of raising the temperature of a heating furnace, which comprises at least one solid electrolyte that separates at least two spaces, up to an operational temperature of the solid electrolyte;
a step of applying a voltage to between electrodes provided on an outer surface and an inner surface of the solid electrolyte and discharging oxygen from the gas in one of the spaces to the gas in the other space using the solid electrolyte;
a step of introducing pure oxygen or air at an atmospheric pressure onto a solid electrolyte surface that has been in contact with a gas whose oxygen partial pressure is reduced, to re-oxidize the solid electrolyte surface; and
a step of dropping the temperature of the heating furnace from the solid electrolyte operational temperature; and (8) the method of (7) for using a solid electrolyte for oxygen partial pressure control, wherein the step of raising the temperature comprises an average rate of temperature rise of 3° C./min to 6° C./min, and wherein the step of dropping the temperature comprises an average rate of temperature drop of 3° C./min to 6° C./min.

The present invention can adopt the following apparatus structures if the process gas requires an even lower oxygen partial pressure: the oxygen partial pressure control apparatus of (1) in the present invention, comprising a second heating furnace housing a second oxygen pump comprising a tubular solid electrolyte, where the solid electrolyte in the second oxygen pump is connected between the aforementioned oxygen pump and the aforementioned oxygen sensor, and where a purge gas that sweeps the surroundings of the tube is an inert gas with a controlled oxygen partial pressure; or, the oxygen partial pressure control apparatus of (1) in the present invention, in which the tubular structure of the aforementioned oxygen pump is a double-tubed structure comprising an outer tube and a coaxial inner tube, and in the space between the inner tube and the outer tube, a process gas whose oxygen partial pressure has been reduced by the solid electrolyte of the outer tube is guided in to the space in the inner tube, so that its oxygen partial pressure is further reduced by the solid electrolyte of the inner tube.

| | |
|---|---|
| 1 | Heating furnace |
| 2 | Zirconium tube |
| 3 | Flange |
| 4 | Inner surface porous electrode |
| 5 | Outer surface porous electrode |
| 6 | Inner surface platinum wire electrode |
| 7 | Outer surface platinum wire electrode |
| 8 | Cooling means |
| 9 | Resistive heating element |
| $F_{in}$ | External processing apparatus gas supply tube |
| $F_{out}$ | External processing apparatus gas exhaust tube |
| $G_{in}$ | Supply of argon (Ar) gas flow |

BEST MODE FOR CARRYING OUT THE INVENTION

Figure 1:
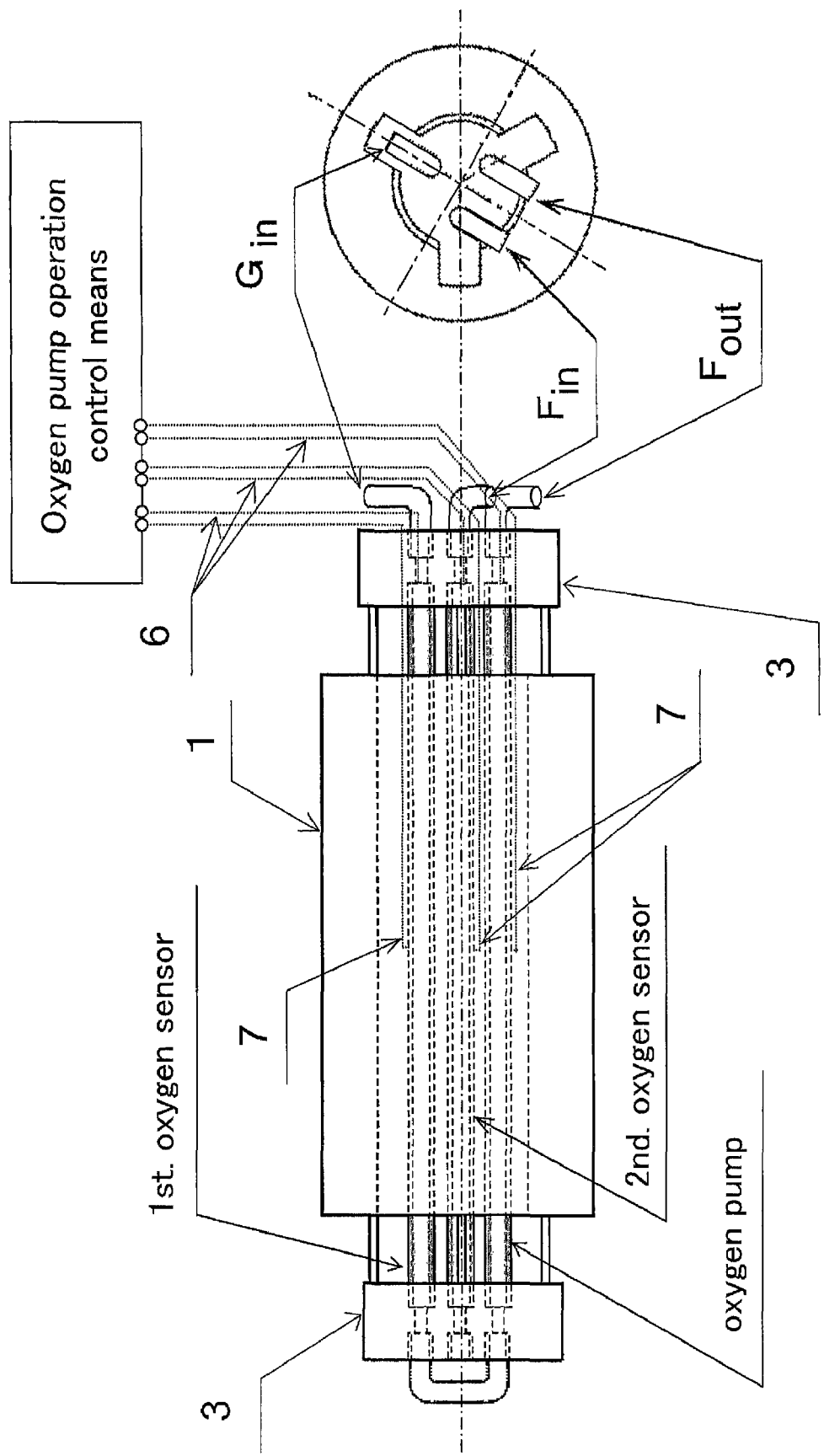
FIG. 1 shows a general overview of an oxygen partial pressure control apparatus of the present invention.

FIG. 1 shows a general sectional overview of an oxygen partial pressure control apparatus of the present invention, particularly, a heating furnace and its surroundings. FIG. 1 (left) is a sectional view of one side of an apparatus, as viewed in the axial direction of the solid electrolytes. FIG. 1 (right) is a sectional view of the front of the apparatus. Each cross section shows a surface cut along the dashed line in the other figure.

Herein, in a tubular heating furnace 1, solid electrolyte tubes 2 for an oxygen pump, a first oxygen sensor, and a second oxygen sensor are arranged in parallel at equal intervals via a pair of flanges 3. Each solid electrolyte tube is mounted such that both ends project out from the heating furnace.

FIG. 1 has adopted a structure in which both ends of the furnace are open to the air, but they may also be airtight. In this case, a structure can be adopted in which a purge gas introduction hole is formed in the center of one side of a flange; a supply flow of purge gas comprising pure oxygen or air is introduced via this introduction hole; the heating furnace is swept to maintain a constant external atmosphere for the aforementioned solid electrolyte tube in heating furnace 1; and an exhaust flow of purge gas is discharged through a purge gas discharge hole formed in the other end of the flange. The flow rate of the purge gas is preferably 2,300 sccm to 3,400 sccm per liter of heating furnace volume.

Herein, as the solid electrode constituting the aforementioned oxygen pump, for example, a zirconium system expressed by the general formula $(ZrO_2)1-x-y(In_2O_3)x(Y_2O_3)y$ ($0<x<0.20$, $0<y<0.20$, $0.08<x+y<0.20$) can be used. Alternatively, a composite B oxide can also be used, where the composite B oxide comprises Ba and In, with Ba in the composite oxide partly replaced with La and particularly having a molar ratio $\{La/(Ba+La)\}$ of 0.3 or more; or that where In is partly replaced with Ga; or that expressed by the general formula $\{Ln_{1-x}S_xGa_{1-(y+z)}Mg_yCo_zO_3$ where Ln=one or both of La and Nd, x=0.05 to 0.3, y=0 to 0.29, z=0.01 to 0.3, y+z=0.025 to 0.3); or that expressed by the general formula $(\{Ln_{(1-x)}A_xGa_{(1-y-z)}B1_yB2_zO_3-d$, where Ln=one or two or more of La, Ce, Pr, Nd, and Sm, A=one or two or more of Sr, Ca, and Ba, B1=one or two or more of Mg, Al, and In, B2=one or two or more of Co, Fe, Ni, and Cu}; or that expressed by the general formula $\{Ln_{2-x}M_xGe_{1-y}L_yO_5$, where Ln=La, Ce, Pr, Sm, Nd, Gd, Yd, Y, Sc, M=one or two or more of Li, Na, K, Rb, Ca, Sr, and Ba, L=one or two or more of Mg, Al, Ga, In, Mn, Cr, Cu, and Zn}; or that expressed by the general formula $\{La_{(1-x)}SrxGa_{(1-y-z)}Mg_yAl_2O_3$, where $0<x\leq0.2$, $0<y\leq0.2$, $0<z<0.4\}$; or that expressed by the general formula $\{La_{(1-x)}A_xGa_{(1-y-z)}B1_yB2_zO_3$, where Ln=one or two or more of La, Ce, Pr, Sm, and Nd, A=one or two or more of Sr, Ca, and Ba, B1=one or two or more of Mg, Al, and In, B2=one or two or more of Co, Fe, Ni, and Cu, x=0.05 to 0.3, y=0 to 0.29, z=0.01 to 0.3, y+z=0.025 to 0.3\}$. An electrochemical oxygen pump equipped with a solid electrolyte comprising such an oxide ion conductor may be used alone; however, for example, it can also be used in combination with a getter material to promote the control of oxygen partial pressure.

The inner and outer peripheral surfaces of a tubular solid electrolyte comprising an above material are equipped with electrodes in the form of a net or such and composed of platinum or the like. Applying a current from a DC power source to these electrodes causes the solid electrolytes to electrically reduce oxygen molecules comprised in the gas in the solid electrolyte tube, and the resulting oxygen ions are incorporated into the solid electrolyte. Meanwhile, the oxygen ions are released from the outer surfaces of the solid electrolyte tube as oxygen molecules, which are discharged to the outside of the system using a purge gas which flows outside the tube.

Figure 2:
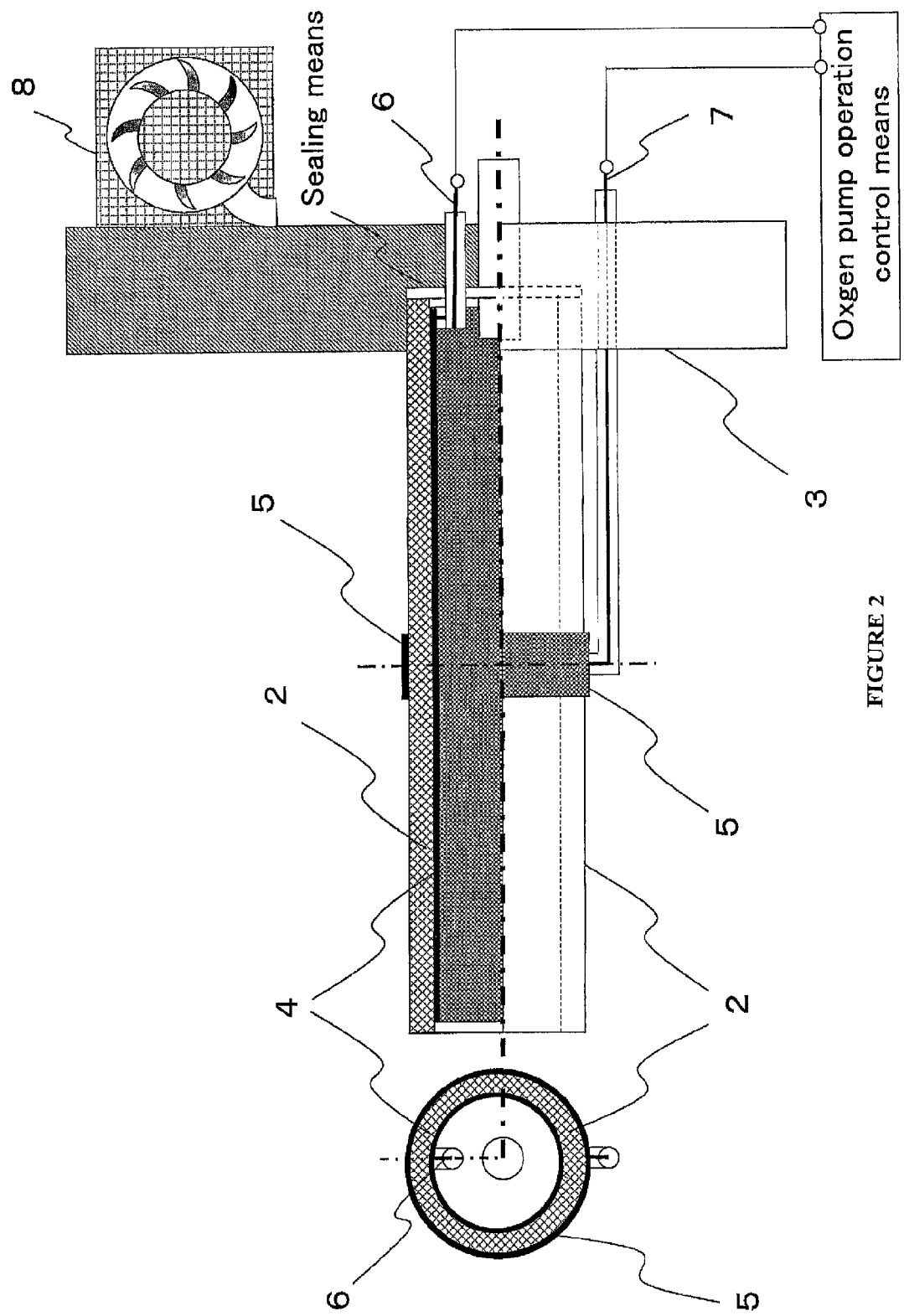
FIG. 2 shows an electrode structure of an oxygen sensor and a sealing structure at one end of a solid electrolyte of the present invention.

To reduce the material costs of the solid electrolyte tube 2 for the oxygen pump and oxygen sensors, the length protruding from the heating furnace was reduced by 7 cm, such that the solid electrolyte tube was 20 cm long. As a result, the tube's end becomes hot due to heat conducted through the solid electrolytes, and as a countermeasure, an air cooling fan 8 was provided near the solid electrolyte tube to cool the sealing mechanism at the tube's end. FIG. 2 is a schematic diagram showing the peripheral structure of a solid electrolyte tube for an oxygen sensor. Herein, an air cooling scheme was adopted; however, other cooling means may also be adopted.

Platinum electrodes 4 and 5 are provided on the inner and outer surfaces of the solid electrolyte tube 2 of the oxygen sensor. To avoid the effects of a temperature gradient in the hot parts of the zirconium tube operating as a solid electrolyte, the following configuration is preferable: as shown in FIG. 2, a platinum paste is applied over the entire inner surface and then baked such that the entire inner surface forms an inner surface porous electrode 4. A platinum wire 6 is then adhered thereto. For the outer surface, platinum paste is applied only to a band-like area about 1 to 2 cm wide, near the center of solid electrolyte 2, and is then baked to form an outer surface porous electrode 5. A platinum wire 7 is then inserted through an insulating glass tube and adhered to outer surface electrode 5. The platinum wire 7 is then pulled out of the furnace, and the difference in electrical potential between the aforementioned platinum wire 6 is measured. This structure eliminates the need for calibration of each oxygen sensor and the oxygen partial pressure can be calculated directly from the Nernst's equation, which is based on thermodynamics.

EXAMPLES

Example 1

In the present Example, in particular, the solid electrolyte tube 2 for the oxygen pump, the solid electrolyte 2 for the first oxygen sensor, and the solid electrolyte 2 for the second oxygen sensor were arranged in parallel so that the axes of each solid electrolyte tube 2 match with each vertex of the equilateral triangles. Since the flanges 3 were open type, the oxygen pump, first oxygen sensor, and second oxygen sensor were installed in the same atmosphere.

Then, 200 sccm of argon gas was introduced into solid electrolyte tube 2 of the oxygen pump. A voltage of −2 V to 2 V was applied between the electrodes inside and outside of solid electrolyte 2 of the oxygen pump, depending on the feedback gain. The heating furnace adopted in the present Example was open type and this was carried out in air; however, a closed type furnace may also be adopted and pure oxygen may be used as a purge gas.

Figure 3:
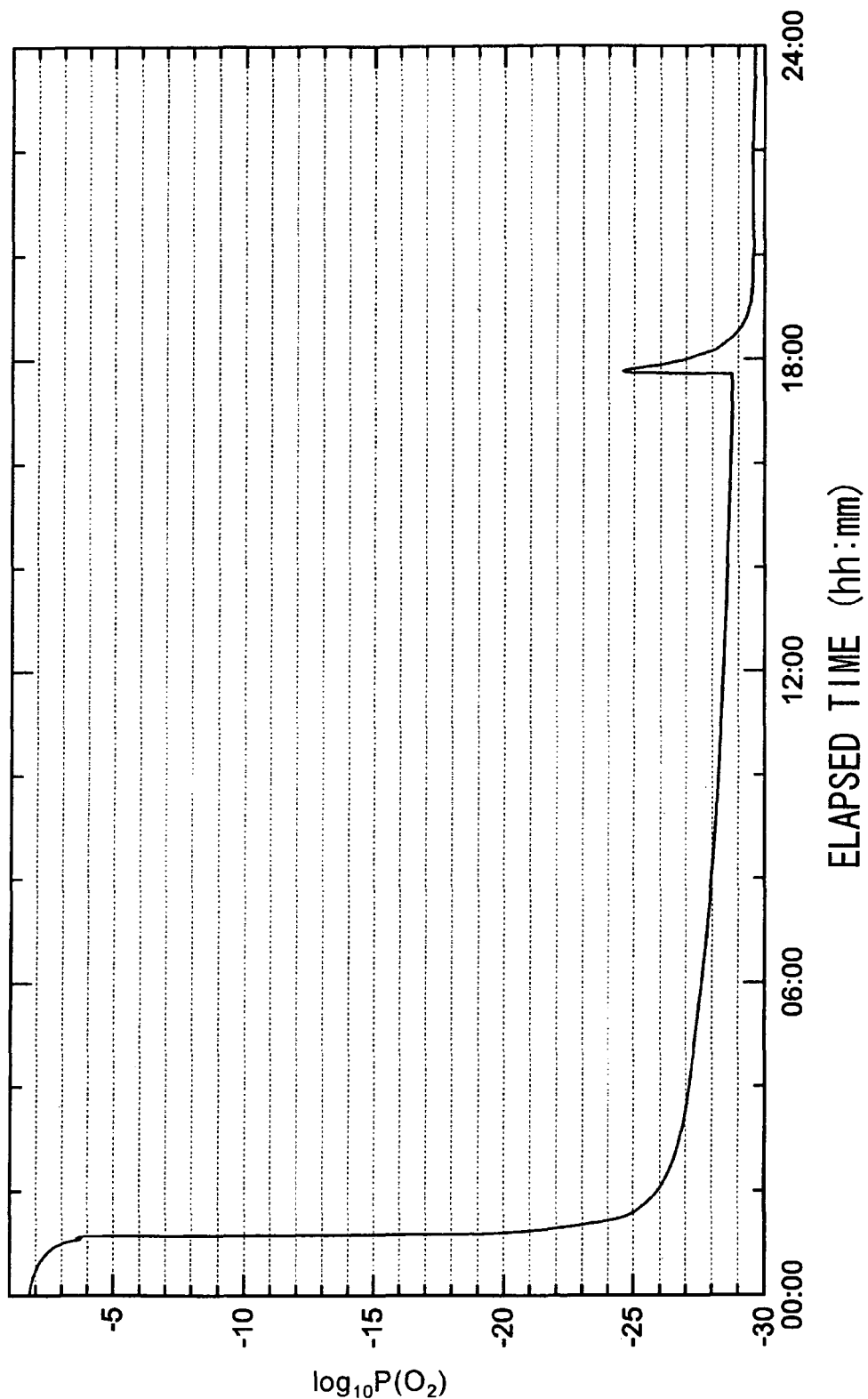
FIG. 3 shows an example of the oxygen partial pressure behavior of a gas processed by an oxygen partial pressure control apparatus of the present invention.

Then, argon gas that had passed through solid electrolyte tube 2 of the oxygen pump and whose oxygen partial pressure had been reduced was then guided into solid electrolyte tube 2 of the first oxygen sensor, and the partial pressure of oxygen in the argon gas was measured. Oxygen partial pressure was measured using the electromotive force generated by the concentration cell reaction resulting from the difference in oxygen partial pressure between the inside and outside of solid electrolyte tube 2. FIG. 3 shows the variation in oxygen partial pressure over time. The oxygen partial pressure reached about $10^{-26}$ atm in about two hours and stabilized at $10^{-30}$ atm after about 20 hours of operation. In FIG. 3, a small peak was observed around the elapsed time of 18:00; however, its cause is unknown and it was not always reproducible.

Example 2

To meet the needs for mass production of gases with controlled oxygen partial pressure, a design that assembles the heating furnaces of the present invention was advanced to provide an embodiment in which a number of solid electrolyte tubes 2 are placed in one heating furnace.

Figure 4:
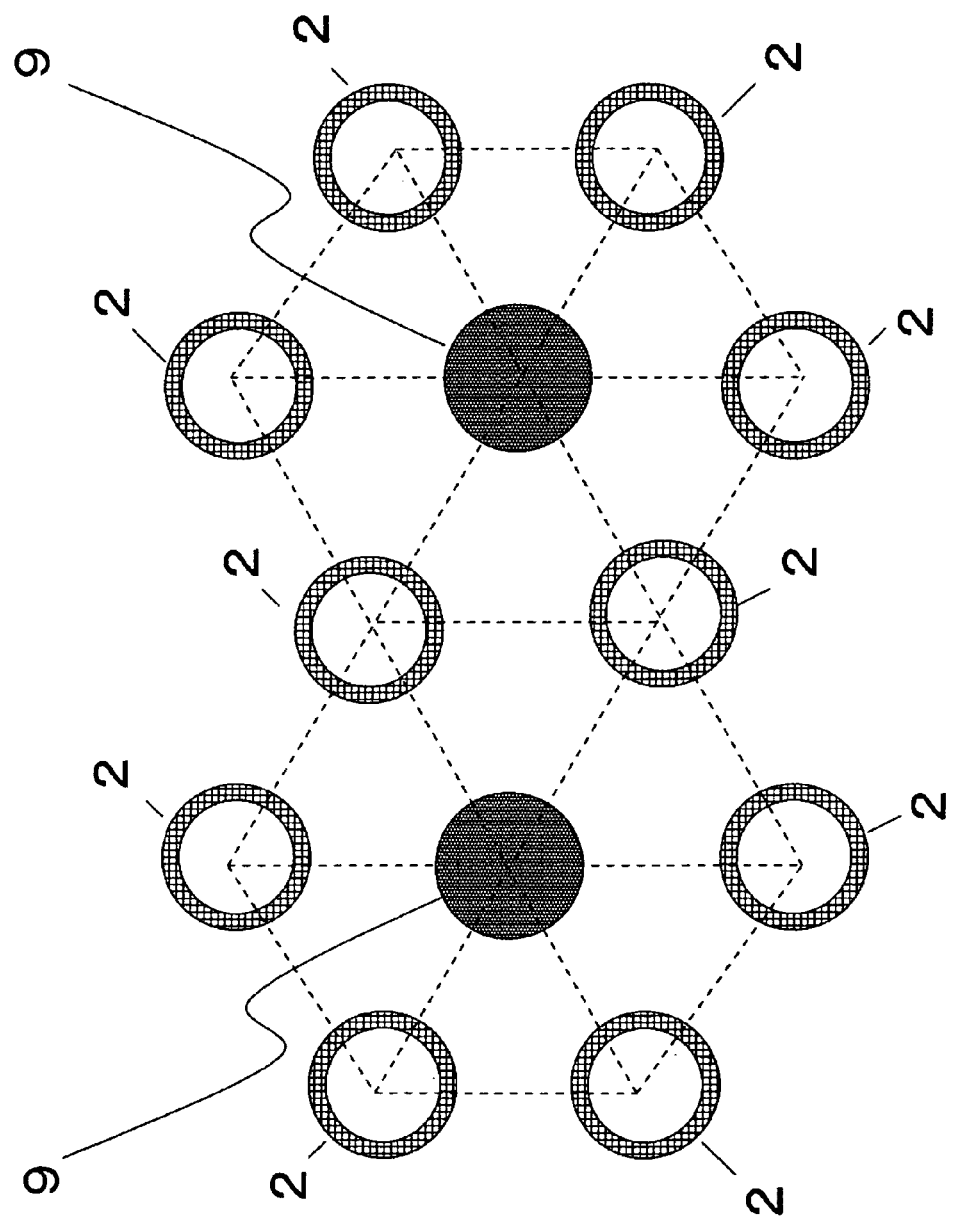
FIG. 4 shows a layout in which oxygen pumps of the present invention are installed.

Solid electrolyte tubes 2 and resistive heating elements 9 were arranged in parallel as shown in FIG. 4. Specifically, the axis of each solid electrolyte 2 was placed at each vertex of a honeycomb structure centered on the axis of the cylindrical resistive heating element 9. This enabled differences in temperature in solid electrolyte tube 2 to be maintained at less than 1° C.

Herein, the layout in FIG. 4 is not limited to these numbers. The layout can of course be further expanded, and the ratio between the number of solid electrolyte tubes 2 and the number of resistive heating elements 9 can also be varied in the range of ⅓ to 6. In FIG. 4, any two solid electrolyte tubes are selected from those described as solid electrolytes 2 for oxygen pumps, and these are used as solid electrolyte tubes for the first and second oxygen sensors.

Example 3

In the present example, to meet the need for a wide range of oxygen partial pressures in atmospheric gases for actual operations, that is, oxygen partial pressures of 0.2 atm to $10^{-30}$ atm, PID control was performed as described below to rapidly control partial pressure to target partial pressures. This successfully reduced operational costs.

Figure 5:
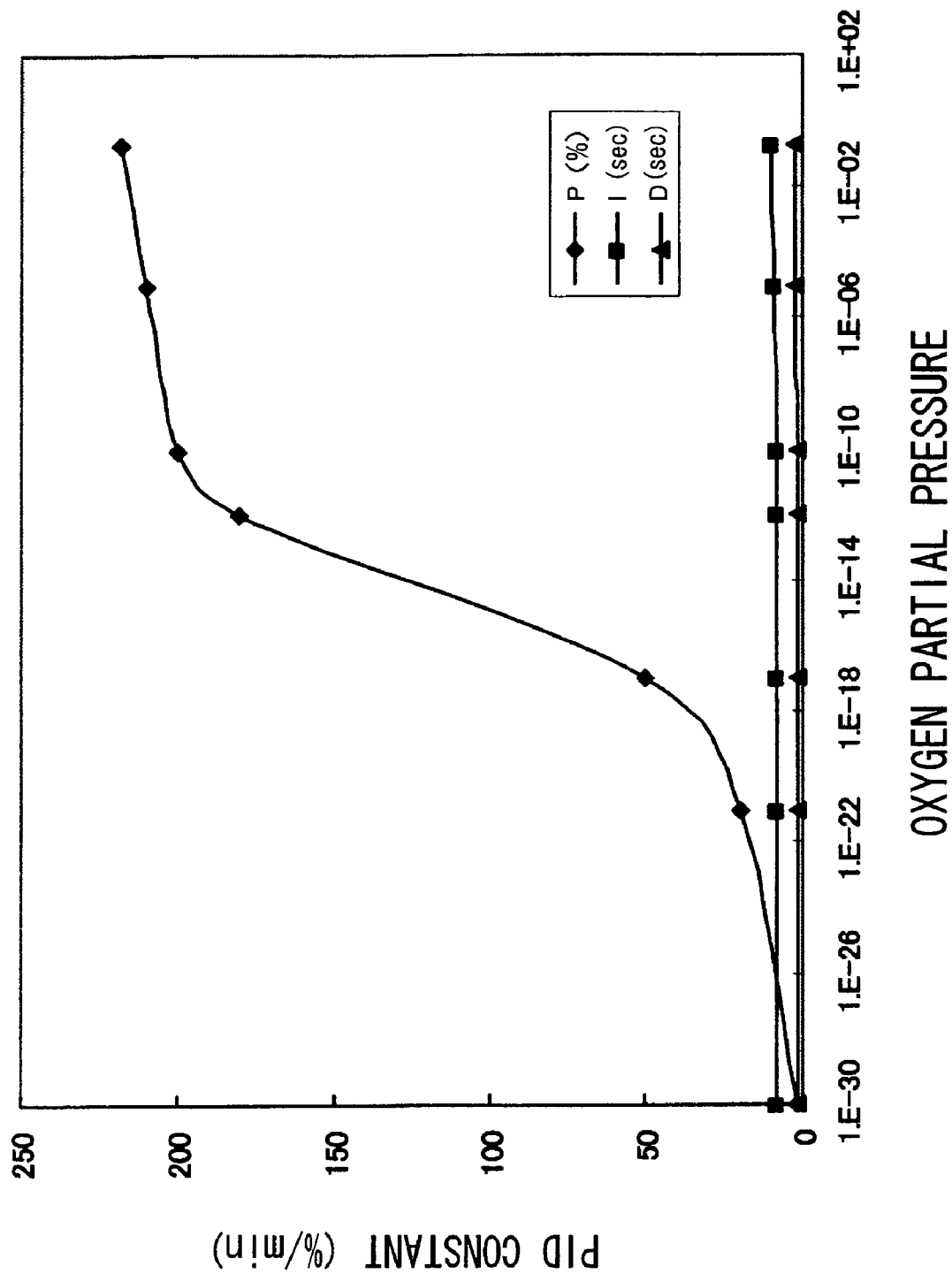
FIG. 5 shows the profile of a PID constant that depends on oxygen partial pressure, adopted for use with the oxygen partial pressure control apparatuses of the present invention.

Specifically, as exemplified in FIG. 5, a design scheme able to smoothly and automatically set a variable PID constant depending on the oxygen partial pressure at a given time was adopted. The table below shows the estimated values of each constant for oxygen partial pressure levels. However, this table does not indicate that the constant varies between multiple levels. For actual operation, the constant is defined as a continuous function based on oxygen partial pressure.

| OXYGEN PARTIAL PRESSURE (atm) | P (%) | I (sec) | D (sec) |
|---|---|---|---|
| 0.2 | 218 | 10 | 2.5 |
| $1.00^{-05}$ | 210 | 9 | 2.2 |
| $1.00^{-10}$ | 200 | 8 | 2 |
| $1.00^{-12}$ | 180 | 8 | 2 |
| $1.00^{-17}$ | 50 | 8 | 2 |
| $1.00^{-21}$ | 20 | 8 | 2 |
| $1.00^{-30}$ | 2 | 8 | 2 |

Figure 6:
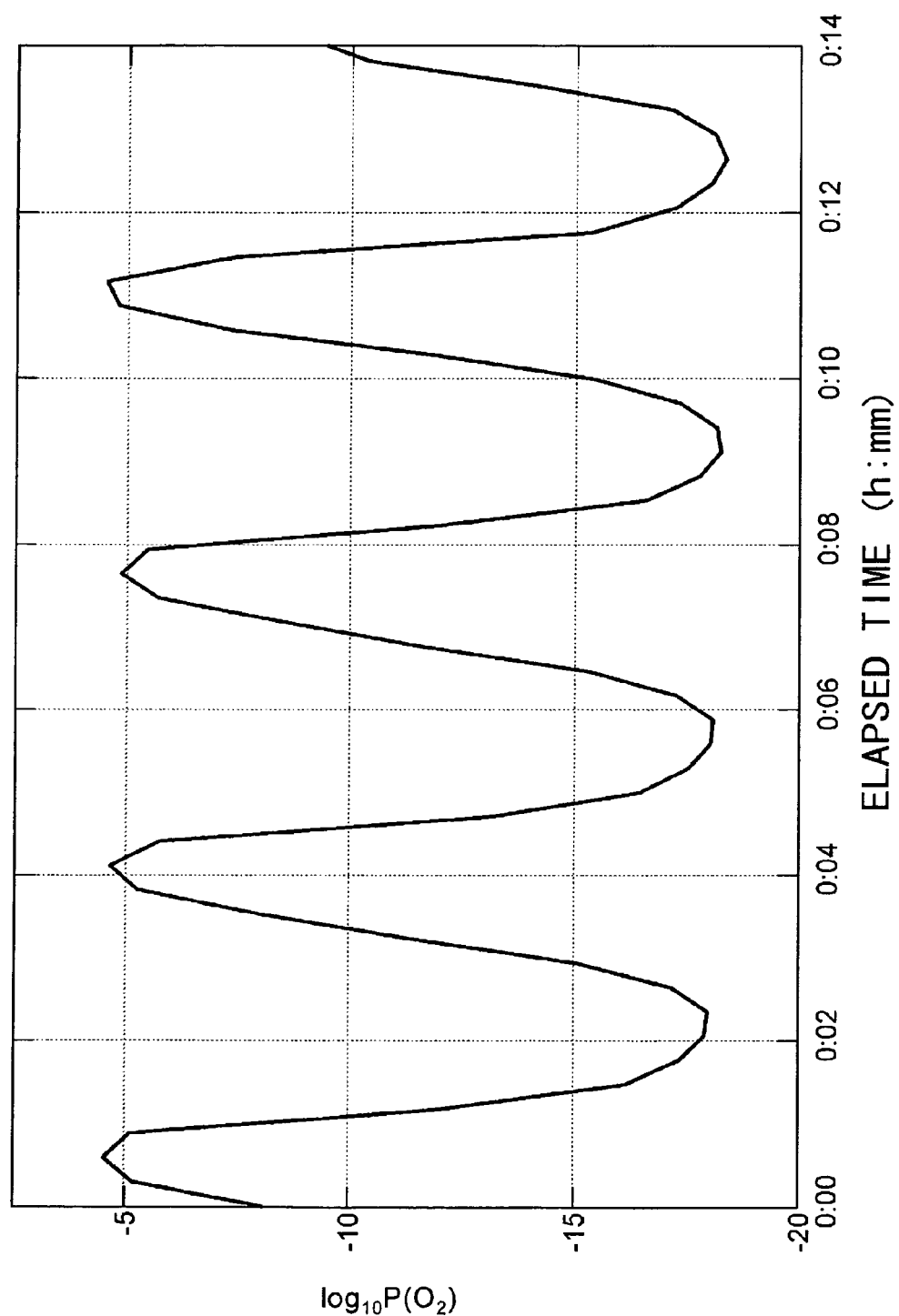
FIG. 6 shows an example of the history of oxygen partial pressure variations observed when the PID constant is fixed for an oxygen partial pressure control apparatus of the present invention.

As a premise for the PID constant in FIG. 5, the apparatus is structured such that the heating furnace has an internal volume of 0.03 L, the zirconium tube has a length of 200 mm and a diameter of 10 mm, and the temperature of operation is 600° C. to 700° C. However, the PID constant is preferably modified to match the apparatus structure adopted. As a reference, FIG. 6 shows the behavior of oxygen partial pressure after the oxygen partial pressure was reduced to $10^{-10}$ atm upon the introduction of pure argon gas into an apparatus with a fixed PID constant, optimized for an oxygen partial pressure of $10^{-20}$ atm. As seen in the Figure, when controlling using a fixed PID constant, the oxygen partial pressure periodically oscillates widely, and a long time is required before a stable oxygen partial pressure is obtained. This behavior is markedly different from that in the case of the aforementioned FIG. 3, where the PID constant varied.

Example 4

Since zirconium tubes are used in harsh environments, namely an oxygen partial pressure of about $10^{-30}$ atm inside the oxygen pump and a temperature of 600° C. to 700° C., the life of a zirconium tube is preferably prolonged by reducing the rate of temperature rise during preparation and the rate of temperature fall at the end of operations as much as permitted by operational efficiency. Further, measures are preferably taken to repair the inner surface of the solid electrolyte partly reduced as a result of extended use under a very low oxygen partial pressure.

Thus, the temperature was controlled such that the average rate of temperature rise or fall was 3° C./min to 6° C./min, so as to slowly raise or drop the temperature between room temperature and an operational temperature of 600° C. to 700° C. over two to three hours. Further, a step is added in which 1 atm of pure oxygen or air is introduced into the solid electrolytes for the oxygen pump and such, after operation of the oxygen pump and before the temperature has started to drop. Specifically, each solid electrolyte tube is preferably provided with an inflow tube for a supply of pure oxygen or air, and an outflow tube for pure oxygen or air to exit the system after circulating in the solid electrolyte tube, such that after operation of the solid electrolyte, the inner surface of the solid electrolyte tube, which was partly reduced under the very low oxygen partial pressure, is re-oxidized by the pure oxygen or air.

Using the above, the life of zirconium tubes could be prolonged, such that zirconium tubes that were damaged after about a week to ten days of normal continuous operation have not been reported as damaged, although more than five months have passed since the start of experiments.

INDUSTRIAL APPLICABILITY

The present invention provides oxygen partial pressure control apparatuses in which sharing a purge gas for solid electrolytes between an oxygen pump and an oxygen sensor allows the solid electrolytes to be compactly housed in one heating furnace, reducing both facility and operational costs.

The present invention also provides methods for using solid electrolytes in oxygen partial pressure control apparatuses, wherein the methods increase the operating life of the solid electrolytes and reduce maintenance costs by adopting operational methods which are more gentle to the solid electrolytes and special final steps when operating the oxygen partial pressure control apparatuses.

The invention claimed is:

1. An oxygen partial pressure control apparatus comprising:
   at least one oxygen pump comprising a solid electrolyte with a tubular structure,
   at least two oxygen sensors, wherein each of said two oxygen sensors comprises comprising a solid electrolyte with a tubular structure,
   a heating furnace which houses the oxygen pump and the oxygen sensors and which can heat and maintain said at least one oxygen pump and said at least two oxygen sensors at an operational temperature, and wherein air or pure oxygen is supplied to the inside of the heating furnace, and
   an oxygen pump operation control means for controlling operation of said oxygen pump based on the oxygen partial pressure detected by said oxygen sensors,
   wherein the oxygen pump and the oxygen sensors are placed in parallel, such that the air or pure oxygen serves as a purge gas that sweeps the surroundings of said at least one oxygen pump and said at least two oxygen sensors, and said at least one oxygen pump and said at least two oxygen sensors are connected such that a common process gas can flow through said at least one oxygen pump and said at least two oxygen sensors, wherein the common process gas whose oxygen partial pressure has been reduced by the oxygen pump can be introduced into the oxygen sensors, and
   wherein said oxygen pump operation control means has a PID (proportional-integral derivative) constant defined as a function of the oxygen partial pressure, and every time either of said at least two oxygen sensors samples a current oxygen partial pressure value, said PID constant is automatically adjusted in coordination with the function to depend on the current oxygen partial pressure, and wherein operation of said oxygen pump is subjected to PID control based on the adjusted PID constant.

2. The oxygen partial pressure control apparatus of claim 1, wherein both ends of the solid electrolyte of said oxygen pump protrude from the heating furnace and are sealed with a sealing means to make said oxygen pump solid electrolyte tubular structure airtight, and further comprising a cooling means for cooling the sealing means.

3. The oxygen partial pressure control apparatus of claim 1 or 2, wherein at least one of the oxygen sensors comprises a porous electrode formed over an entire inner surface of a tubular structure, and a porous electrode formed as a band around an outer periphery of a tubular structure, and wherein at least one of the oxygen sensors measures an oxygen partial pressure by detecting a difference in potential produced between the two electrodes.

4. The oxygen partial pressure control apparatus of claim 1, wherein the heating furnace comprises at least one cylindrical resistive heating element placed in parallel with each of the solid electrolytes with the tubular structure, wherein the ratio between the number of solid electrolytes and the number of resistive heating elements is $1/3$ to 6.

5. The oxygen partial pressure control apparatus of claim 4, wherein the solid electrolytes with the tubular structure are arranged at equal intervals such that the axis of each solid electrolyte with the tubular structure is located at each vertex of a honeycomb structure centered on an axis of the resistive heating element, as viewed in an axial direction of the resistive heating element and the solid electrolytes with the tubular structure.

\* \* \* \* \*

UNITED STATES PATENT AND TRADEMARK OFFICE
CERTIFICATE OF CORRECTION

| | |
|---|---|
| PATENT NO. | : 8,097,138 B2 |
| APPLICATION NO. | : 11/597045 |
| DATED | : January 17, 2012 |
| INVENTOR(S) | : Naoki Shirakawa |

It is certified that error appears in the above-identified patent and that said Letters Patent is hereby corrected as shown below:

Title Page, Item (73) should read:

Assignee: National Institute of Advanced Industrial Science and Technology and STLAB INCORPORATED.

Signed and Sealed this
Seventh Day of August, 2012

David J. Kappos
*Director of the United States Patent and Trademark Office*